(12) United States Patent
Stamm et al.

(10) Patent No.: US 6,410,744 B1
(45) Date of Patent: Jun. 25, 2002

(54) CARBONYLDIIMIDAZOLES, THEIR ESTER DERIVATIVES AND METHOD FOR THEIR PRODUCTION

(75) Inventors: Armin Stamm, Mainz; Manfred Julius, Limburgerhof; Alois Kindler, Hassloch; Michael Henningsen, Frankenthal; Jörg Botzem, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/445,409
(22) PCT Filed: Jun. 10, 1998
(86) PCT No.: PCT/EP98/03516
§ 371 (c)(1), (2), (4) Date: Dec. 8, 1999
(87) PCT Pub. No.: WO98/56769
PCT Pub. Date: Dec. 17, 1998

(30) Foreign Application Priority Data

Jun. 12, 1997 (DE) .......................................... 197 24 884

(51) Int. Cl.$^7$ ..................... C07D 233/60; C07D 233/80
(52) U.S. Cl. ................. 548/313.7; 548/334.1
(58) Field of Search ............................ 548/313.7, 334.1

(56) References Cited

U.S. PATENT DOCUMENTS

| | | | | |
|---|---|---|---|---|
| 3,121,707 A | * | 2/1964 | Anderson et al. ..... | 548/313.7 X |
| 3,646,048 A | * | 2/1972 | Wright et al. ........ | 548/313.7 X |
| 5,145,983 A | * | 9/1992 | West ................... | 548/313.7 X |
| 5,162,565 A | | 11/1992 | Desmurs .............. | 558/276 |

FOREIGN PATENT DOCUMENTS

| | | |
|---|---|---|
| EP | 236 888 | 9/1987 |
| EP | 468 404 | 2/1992 |
| EP | 692 476 | 1/1996 |
| JP | 41-18585 | * 10/1966 |
| JP | 61-112056 | * 5/1986 |
| JP | 2-207073 | * 8/1990 |

OTHER PUBLICATIONS

J. Org. Chem., Bd 40, 1975, Loozen et al. 3279–3280.
Spec Chem 13, (1993), Damle et al.
Chem. Ber., Bd. 68, 1935, John 2283–2291.
Liebigs Ann. Chem 716, 175 185 (1968) Schanebel et al.
Helv. Chim. Acta Bd., XLIV, Nr. VII 1961, Klee et al. 2151.

* cited by examiner

*Primary Examiner*—Floyd D. Higel
(74) *Attorney, Agent, or Firm*—Keil & Weinkauf

(57) ABSTRACT

Carbonyldiimidazoles of the formulae Ia, Ib, Ic or mixtures thereof

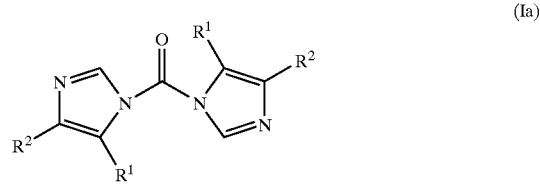

(Ia)

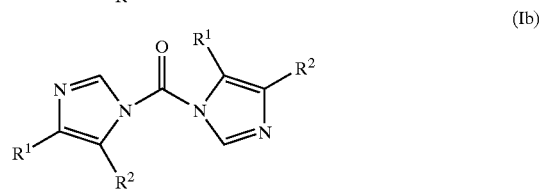

(Ib)

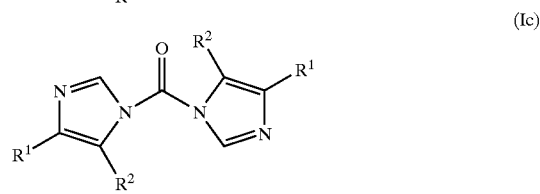

(Ic)

where $R^1$ is $C_{1-4}$-alkyl and $R^2$ is hydrogen or methyl, and tert-butyl esters derived therefrom are described.

4 Claims, No Drawings

CARBONYLDIIMIDAZOLES, THEIR ESTER DERIVATIVES AND METHOD FOR THEIR PRODUCTION

The invention relates to certain carbonyldiimidazoles, esters derived therefrom, processes for their preparation and their use.

In the synthesis of peptides from amino acids, protection of the functional groups not involved in the reaction is absolutely necessary in order to obtain a homogeneous product. One of the most important protective groups, which is also used industrially, for the amino group of amino acids is the tert-butyloxycarbonyl group, which is usually abbreviated to BOC. In this case, the amino functionality is protected as urethane, and the protective group can be eliminated again under mild acidic conditions.

Urethanes are normally prepared by reacting amino groups with a chloroformate. However, tert-butyl chloroformate is extremely unstable and thus can be handled only with difficulty. It is therefore unsuitable for introducing the BOC protective group. Numerous compounds intended to be used to protect amino groups with BOC are described in the literature.

The compound used most often for introducing BOC protective groups is di-tert-butyl dicarbonate, also referred to as di-tert-butyl pyrocarbonate or BOC anhydride $((CH_3)_3C-O-CO-O-CO-O-C(CH_3)_3)$. Processes for preparing BOC anhydride are disclosed, for example, in U.S. Pat. Nos. 5,162,565 and 5,162,565 and EP-A-0 468 404. The processes for preparing BOC anhydride are multistage and include elaborate steps using costly chemicals. This is why BOC anhydride is very costly and is reluctantly employed as compound in industrial reactions.

One example of other compounds for introducing the BOC protective group is BOC fluoride as described in Liebigs Ann. Chem. 716 (1968) 175–185.

J. Org. Chem. 50 (1985) 3951–3953 describes the preparation of 1,2,2,2-tetrachloroethyl tert-butyl carbonate and its use for introducing BOC protective groups.

Helv. Chim. Acta 44 (1961), 2151, Spec. Chem. 13 (1993), 67–69 and EP-A-0 236 888 describe the preparation of tert-butyloxycarbonylimidazole from carbonyldiimidazole and its use for introducing the BOC protective group.

Whereas BOC fluoride can be synthesized only via carbonyl fluoride chloride, which is elaborate to prepare, and therefore has only minor importance, the two other compounds are solids which require elaborate techniques for isolation and purification. Other BOC-introducing reagents have no industrial importance because of their instability.

It is an object of the present invention to provide compounds for introducing BOC protective groups which can be obtained via less elaborate steps from compounds which are easy to obtain. The compounds should furthermore be liquid at room temperature and be amenable to distillation without decomposition under reduced pressure. They should furthermore have a long shelf life and avoid the disadvantages of known compounds.

We have found that this object is achieved by imidazolecarboxylic esters of the formulae IIIa and IIIb or mixtures thereof

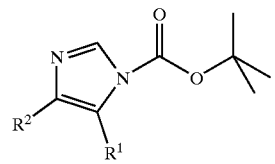
(IIIa)

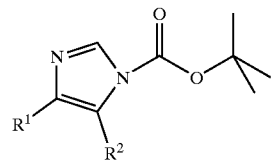
(IIIb)

where $R^1$ is $C_{1-4}$-alkyl and $R^2$ is hydrogen or methyl.

The imidazolecarboxylic esters of the formulae IIIa, IIIb or mixtures thereof can be prepared by reacting carbonyldiimidazoles of the formulae Ia, Ib, Ic or mixtures thereof

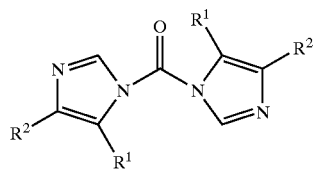
(Ia)

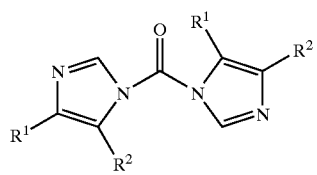
(Ib)

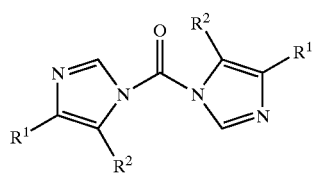
(Ic)

where $R^1$ is $C_{1-4}$-alkyl and $R^2$ is hydrogen or methyl, with tert-butanol in a substituted aromatic hydrocarbon as solvent, and extracting the resulting reaction mixture with water to remove imidazoles of the formulae IIa and IIb

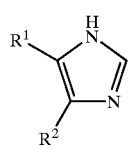
(IIa)

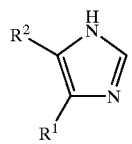
(IIb)

where $R^1$ und $R^2$ have the abovementioned meanings, which are also formed.

The carbonyldiimidazoles of the formulae Ia, Ib, Ic or mixtures thereof can be obtained by reacting at least one imidazole of the formulae IIa and IIb with phosgene in a substituted aromatic hydrocarbon as solvent, wherein the hydrochloride, which is also formed, of the at least one imidazole of the formulae IIa and IIb is removed from the reaction mixture by phase separation as melt.

The preparation of carbonyldiimidazole from imidazole and phosgene is generally disclosed in EP-A-0 692 476. However, the reaction (see Example 1) results in imidazole hydrochloride as solid, which has to be filtered off. This requires a transfer of the reaction mixture, which is disadvantageous because the carbonyldiimidazole which is formed is very moisture-sensitive, and the workup is made difficult for this reason.

It has been found according to the invention that the hydrochlorides of the imidazoles of the formulae IIa and IIb result as liquids (melt) under the reaction conditions and can therefore be removed virtually completely from the product mixture by a simple phase separation. The hydrochlorides obtained in this way can be converted back by neutralization into the imidazoles of the formulae IIa and IIb and returned to the synthesis.

Thus, compared with the process described in EP-A-0 692 476, the removal of the hydrochloride is considerably simplified, and the risk of decomposition of the required carbonyldiimidazoles is reduced.

The carbonyldiimidazoles of the formulae Ia, Ib and Ic are formed as mixture on reaction of imidazoles of the formulae IIa and/or IIb. A shift of the double bonds and protons in the imidazoles is possible during the reaction, so that a product mixture is obtained even from a single compound of the formulae IIa and IIb. However, the product predominantly obtained is the one in which no shift of double bond and proton is necessary. The carbonyldiimidazoles of the formulae Ia, Ib, Ic or mixtures thereof can be isolated by precipitation by cooling the reaction mixture. However, they can also be further processed directly in the reaction mixture, after removal of the hydrochlorides of the imidazoles, without isolation being necessary. It is moreover possible to employ the hot crude solution without further workup.

The carbonyldiimidazoles of the formulae Ia, Ib, Ic or mixtures thereof can be employed for a large number of reactions, for example for preparing corresponding tert-butyl imidazole-1-carboxylates, for carbonyl group transfer, or for dehydration, especially for preparing esters and amides from carboxylic acids.

As a rule, phosgene is passed into the at least one imidazole of the formulae IIa and IIb in the solvent at from 60 to 130° C., preferably 80 to 130° C., in particular 90 to 130° C. Solvents which can be used are all substituted aromatic hydrocarbons suitable for this purpose. Examples of preferably employed solvents are chlorobenzene, xylene and o-dichlorobenzene. Unreacted phosgene can be removed by stripping with inert gases such as nitrogen. The resulting reaction mixture can if necessary be heated further until a liquid two-phase system forms and phase separation becomes possible.

Conversion of the carbonyldiimidazoles of the formulae Ia, Ib, Ic or mixtures thereof into the imidazolecarboxylic esters of the formulae IIIa and IIIb or mixtures thereof takes place by reaction with tert-butanol in a substituted aromatic hydrocarbon as solvent. This preferably entails employing a solvent as defined previously, which is, in particular, identical to the solvent used in the first reaction step. The reaction mixture obtained in the first reaction step can thus be used further without removing the solvent. The reaction with tert-butanol preferably takes place at from 50 to 140° C., particularly preferably 60 to 120° C., in particular 70 to 90° C. The yield can in this case be increased at a lower temperature. On reaction of carbonyldiimidazoles of the formulae Ia, Ib, Ic or mixtures thereof with tert-butanol there is formation not only of the required tert-butyl esters but also of imidazoles of the formulae IIa and IIb. These imidazoles can be removed by extracting the resulting reaction mixture with water. They can then be isolated from the aqueous imidazole phase and be returned to the process for preparing the carbonyldiimidazoles.

It has been found according to the invention that the resulting reaction mixture can be extracted with water without decomposition (hydrolysis) of the imidazolecarboxylic esters of the formulae IIIa, IIIb or mixtures thereof. Simple extraction with water is therefore possible, with the required imidazolecarboxylic esters being retained in the organic phase. After the solvent has been distilled off under reduced pressure, they can be fractionally distilled in order to obtain the pure imidazolecarboxylic esters of the formulae IIIa, IIIb or mixtures thereof.

The invention also relates to a process for removing imidazoles from reaction mixtures which contain imidazoles of the formulae IIa and IIb or mixtures thereof and imidazolecarboxylic esters of the formulae IIIa and IIIb or mixtures thereof by extracting the reaction mixture with water.

The imidazolecarboxylic esters of the formulae IIIa, IIIb or mixtures thereof can also be prepared by reacting at least one imidazole of the formulae IIa and IIb with di-tert-butyl pyrocarbonate (BOC anhydride). The byproducts produced in this case are carbon dioxide and tert-butanol. However, the process described previously is preferred according to the invention because of the high costs of BOC anhydride.

In the compounds of the above formulae, $R^1$ is $C_{1-4}$-alkyl and $R^2$ is hydrogen or methyl. It is preferred for $R^1$ to be $C_{1-4}$-alkyl and $R^2$ to be hydrogen. In this connection, $R^1$ can be methyl, ethyl, n-propyl, i-propyl, n-butyl, i-butyl, or tert-butyl. $R^1$ is preferably $C_{1-3}$-alkyl, in particular methyl or ethyl, specifically methyl.

The specifically preferred carbonyldiimidazoles of the formulae Ia, Ib, Ic are thus carbonyldi-4-methylimidazole, carbonyl-4-methylimidazole-5-methylimidazole and carbonyldi-5-methylimidazole. The imidazoles of the formulae IIa and IIb employed in these cases are 4-methylimidazole and 5-methylimidazole. 4-Methylimidazole is particularly preferably employed in the synthesis. In this case, carbonyldi-4-methylimidazole is mainly obtained.

Reaction of the isomeric carbonyldimethylimidazoles with tert-butanol results in tert-butyl 5- and 4-methylimidazole-1-carboxylates as imidazolecarboxylic esters of the formulae IIIa, IIIb. When 4-methylimidazole is exclusively used originally it is mainly the 4-methylimidazole isomer which is obtained. The content of the 5-methylimidazole isomer is about 6 to 7%. The product mixture can be distilled without decomposition at a boiling point of about 63–64° C. under 0.4 bar.

The imidazolecarboxylic esters of the formulae IIIa and IIIb or mixtures thereof can be used to introduce BOC protective groups into amino functionalities. A general process for this is described in Spec. Chem. 13 (1993), 67–69. This entails compounds containing amino functionalities being reacted with imidazolecarboxylic esters of the formulae IIIa and IIIb or mixtures thereof. The imidazoles are liberated again during this, so that homogeneous protective groups are obtained, irrespective of the carboxylic ester isomer employed.

It is possible in the process according to the invention to prepare the imidazolecarboxylic esters of the formulae IIIa, IIIb and mixtures thereof, which are liquid at room temperature and can easily be distilled, from chemicals which are easily obtainable at reasonable cost in a one-pot process without workup of the intermediate.

The invention is explained in detail by means of examples hereinafter.

EXAMPLES

Example 1

Preparation of carbonyldi-4-methylimidazole 2 mol of 4-methylimidazole were dissolved in chlorobenzene which had been dehydrated by partial distillation. Then, at 60° C., 0.5 mol of phosgene was passed in (until the phosgene refluxed). Reaction was allowed to continue for 1 h after the introduction was complete, and then the excess phosgene was stripped off with nitrogen. The suspension which had formed was heated at 80 to 100° C. until the lower phase was completely molten. The lower phase was then completely removed. It contained exclusively methylimidazole hydrochloride.

The upper phase contained the carbonyldi-4-methylimidazole, which crystallized out incompletely on cooling. Carbonyldi-4-methylimidazole can be either isolated by evaporating the solvent under reduced pressure or directly processed further in solution. The carbonyldi-4-methylimidazole always contains a proportion of isomeric carbonyl-4-methylimidazole-5-methylimidazole, which arises due to phosgene reacting with the other N atom. This is unimportant for further use of the product because on use to protect the appropriate amino acid no imidazole residue remains in the target molecule.

Melting point of the carbonyldi-4-methylimidazole: 101–107° C.

Yield after isolation: 89%

IR: Carbonyl band at 1717 $cm^{-1}$ Calculated for $C_9H_{10}N_4O$: C, 56.83; H, 5.30 N, 29.46. Found: C, 56.50; H, 5.30 N, 29.60.

Example 2

Preparation of tert-butyl 4-methylimidazole-1-carboxylate 2 mol of 4-methylimidazole were dissolved in xylene which had been dehydrated by partial distillation. Then, at 60° C., 0.5 mol of phosgene was passed in (until the phosgene refluxed). Reaction was allowed to continue for 1 h after the introduction was complete, and then the excess phosgene was stripped off with nitrogen. The suspension which had formed was heated at 130° C. until the lower phase was completely molten. The lower phase was completely removed.

The xylene solution of the carbonyldi-4-methylimidazole (upper phase) was mixed with an equimolar amount of tert-butanol and refluxed for 2 hours. Conversion was checked by GC. (Formation of 4-methylimidazole and tert-butyl 4-methylimidazole-1-carboxylate, disappearance of the tert-butanol and carbonyldi-4-methylimidazole band).

After conversion was complete, the reaction solution was extracted twice with water in order to remove the 4-methylimidazole from the solution.

The organic phase was fractionally distilled. The product (tert-butyloxycarbonyl-4-methylimidazole) distilled at 63–64° C. and 0.4 mbar.

IR: Carbonyl band at 1752 $cm^{-1}$ Calculated for $C_9H_{14}N_2O_2$: C, 59.32; H, 7.74; N, 15.37. Found: C, 59.10; H, 7.60; N 15.50.

The product contains a proportion of isomeric tert-butyl 5-methylimidazole-1-carboxylate (6 to 7%). This is of no importance for use as protective group reagent because there is exclusive transfer of the BOC group.

Example 3

Alternative Synthetic Route 47.96 g (0.22 mol) of di-tert-butyl pyrocarbonate (BOC anhydride) were added over the course of about 1 minute to a solution of 16.4 g (0.2 mol) of 4-methylimidazole and 1.2 g (0.01 mol) of 4-dimethylaminopyridine (DMAP) in 250 ml of dry acetonitrile under $N_2$ and while stirring at 18° C. The reaction solution was warmed to 22° C. over the course of 5 minutes, and it was then stirred for 1 hour. After concentration in a rotary evaporator at 45° C. under 10 to 20 mbar, 37.5 g of liquid residue remained and were subjected to short-path distillation under 1 mbar.

At a bottom temperature of 82° C. and an overhead temperature of 65° C., 28.0 g of main distillate were obtained as clear, mobile liquid which had the following composition according to GC and NMR analyses:

83.0% tert-butyl 4-methylimidazole-1-carboxylate, 11.0% tert-butyl 5-methylimidazole-1-carboxylate The initial distillate (6.5 g) contained a further 5.4 g of tert-butyl 4-methylimidazole-1-carboxylate and 0.5 g of tert-butyl 5-methylimidazole-1-carboxylate. (Distillation residue: 0.7 g).

The total yield of tert-butyl 4-methylimidazole-1-carboxylate was thus 32.2 g (0.18 mol), 88%.

Example 4

Improved Process 1020 g of chlorobenzene were dehydrated by distilling off 20 g of chlorobenzene. 164 g of 4-methylimidazole (2 mol) were added molten and were dissolved. 50 g (0.5 mol) of phosgene were passed in over the course of 30 minutes at an internal temperature of 60–70° C. Subsequent reaction for one hour was followed by stripping with nitrogen; heating was continued during this until the solid lower phase was completely molten (internal temperature 95° C.). The lower phase was then separated off at 95° C. (156 g).

74 g (1 mol) of tert-butanol were added dropwise over the course of 10 minutes to the chlorobenzene phase at 82 to 76° C., and the reaction solution was stirred at 80° C. for 5 h. The discharge was extracted twice with 100 ml of water each time. The residue (85 g) after removal of the solvent by distillation under reduced pressure was fractionally distilled. The main fraction distilled at 78–83° C. under 1.5 mbar. 66.2 g of tert-butyl 4-methylimidazole-1-carboxylate were distilled, corresponding to a yield of 72.7%. The product contained about 4% of the 5-methylimidazole isomer.

Example 5

Introduction of the BOC Protective Group on the Amino Group of D,L-alanine 8.9 g of D,L-alanine (0.1 mol), 75 g of DMF and 30.4 g of diazabicycloundecene ("DBU", 0.2 mol) are mixed. 23 g (0.12 mol) of tert-butyl 4-methylimidazole-1-carboxylate are added dropwise over the course of 10 minutes so that the temperature does not rise above 5° C. The mixture is then stirred at room temperature for 20 h. The discharge is adjusted to pH 2.5 with 10% strength HCl at 0–5° C. It is extracted once with methyl tert-butyl ether (MTBE). The organic phase is concentrated under reduced pressure, whereupon the residue partially crystallizes. Suspension with cyclohexane results in colorless crystals of melting point 105–106° C. The NMR spectrum and elemental analysis agree with reference data.

We claim:
1. A process for preparing a carbonyldiimidazole of the formula Ia, Ib, Ic or a mixture thereof

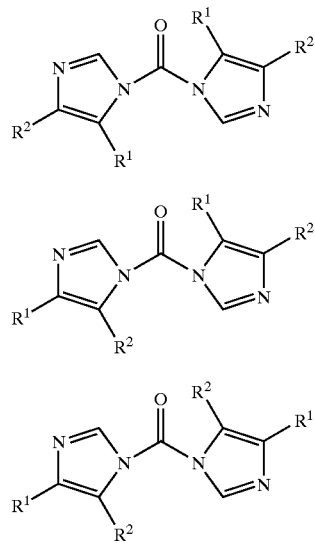

where $R^1$ is $C_{1-4}$-alkyl and $R^2$ is hydrogen or methyl by the reaction of at least one imidazole of the formula IIa or IIb

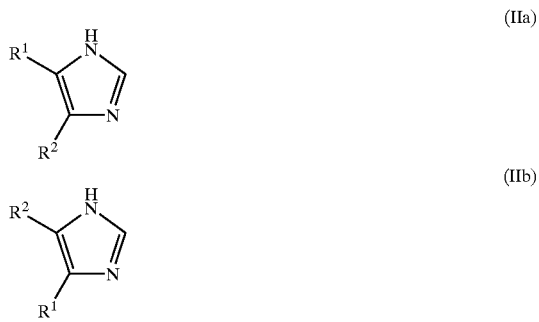

with phosgene in a substituted aromatic hydrocarbon as solvent,
wherein the hydrochloride, which is also formed, of said at least one imidazole of the formula IIa or IIb is removed from the reaction mixture by phase separation as a melt.

2. An imidazolecarboxylic ester of the formula IIIa or IIIb or a mixture thereof

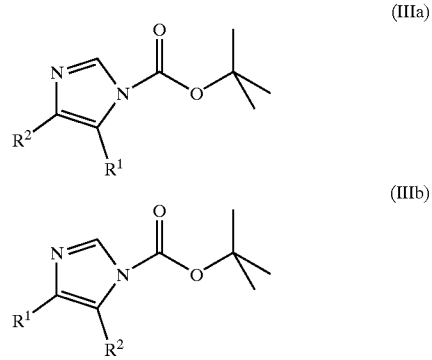

where $R^1$ is $C_{1-4}$-alkyl and $R^2$ is hydrogen or methyl.

3. A process for preparing an imidazolecarboxylic ester of the formula IIIa, IIIB or a mixture thereof as claimed in claim 2 by reacting a carbonyldiimidazole of the formula Ia, Ib, Ic or a mixture thereof

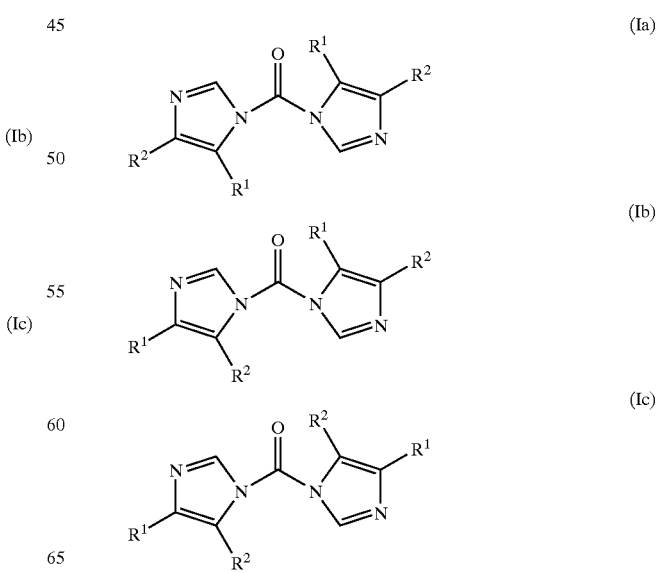

with tert-butanol in a substituted aromatic hydrocarbon as solvent and extracting the resulting reaction mixture with water to remove imidazoles, which are also formed, of the formulae IIa and IIb

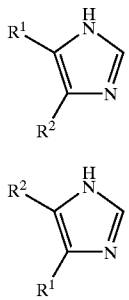

(IIa)

(IIb)

where $R^1$ and $R^2$ have the above meanings.

4. A process for preparing an imidazolecarboxylic ester of the formula IIIa, IIIb or a mixture thereof as claimed in claim 2 by reacting at least one imidazole of the formula IIa or IIb

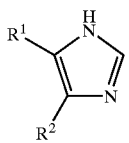

(IIa)

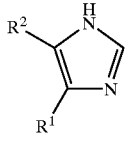

(IIb)

wherein $R^1$ is $C_{1-4}$-alkyl and $R^2$ is hydrogen or methyl with di-tert-butyl pyrocarbonate.

* * * * *